United States Patent [19]

Huffman et al.

[11] Patent Number: 4,976,266

[45] Date of Patent: Dec. 11, 1990

[54] METHODS OF IN VIVO RADIATION MEASUREMENT

[75] Inventors: Dennis D. Huffman; Robert C. Hughes; Charles A. Kelsey, all of Albuquerque, N. Mex.; Richard Lane, Galveston, Tex.; Antonio J. Ricco, Albuquerque, N. Mex.; Jay B. Snelling, Albuquerque, N. Mex.; Thomas E. Zipperian, Albuquerque, N. Mex.

[73] Assignee: United States Department of Energy, Washington, D.C.

[21] Appl. No.: 224,282

[22] Filed: Jul. 25, 1988

Related U.S. Application Data

[62] Division of Ser. No. 901,867, Aug. 29, 1986, abandoned.

[51] Int. Cl.$^5$ .............................................. G01T 1/161
[52] U.S. Cl. ........................................ 128/659; 600/3; 250/370.07; 250/370.14; 250/371
[58] Field of Search .................... 128/613, 654, 659; 600/3; 250/370.01, 370.07, 370.14, 370.15, 371

[56] References Cited

U.S. PATENT DOCUMENTS

| | | |
|---|---|---|
| 3,297,896 | 1/1967 | Anton . |
| 3,427,454 | 2/1969 | Burns et al. . |
| 3,569,704 | 3/1971 | Mitchell ............................... 250/371 |
| 3,569,710 | 3/1971 | Jalink, Jr. ............................ 250/371 |
| 3,598,109 | 8/1971 | Kobayashi et al. . |
| 3,665,916 | 5/1972 | Kobayashi et al. . |
| 3,669,095 | 6/1972 | Kobayashi et al. . |
| 3,670,719 | 6/1972 | Kobayashi et al. . |
| 4,152,595 | 5/1979 | Garfinkel et al. ..................... 250/370 |
| 4,213,045 | 7/1980 | Fraass et al. ......................... 250/370 |
| 4,484,076 | 11/1984 | Thomson ............................. 250/370 |
| 4,605,946 | 8/1986 | Robinson, Jr. .................. 250/370 K |
| 4,757,202 | 7/1988 | East ................................. 250/370.07 |

FOREIGN PATENT DOCUMENTS

| | | |
|---|---|---|
| 1220529 | 7/1966 | Fed. Rep. of Germany . |
| 1614764 | 12/1970 | Fed. Rep. of Germany ... 250/370 F |
| 0010480 | of 1972 | Japan . |

OTHER PUBLICATIONS

Ciarlo, "Mosfet Detector Evaluation", IEEE Trans. Nuc. Sci. vol. 21 No. 1 Feb. 1974 pp. 390-394 (copy in 250/370f).

Aug., "Estimating and Reducing Errors in Mos Dosimeters Caused By Exposure to Different Radiations", IEEE Transactions on Nuclear Science, vol. NS-29, No. 6, Dec. 1982 pp. 2000-2003 (copy in 250/370f).

Kelly et al., Dose Enhancement Effects in Mosfetic Exposed in Typical "Cofacilities", IEEE Trans. on Nuclear Sci. vol. NS-30 No. 6 Dec. 1983 pp. 4388-4393.

Hughes, "Theory of Response of Radiation Sensing Field Effect Transistors" J. Appl. Phys. 58(3) Aug. 1985, pp. 1375-1379.

Adams et al., "The Development of an Mos Dosimetry Unit for Use in Space" IEEE Trans. Nucl. Sci. NS25(6) Dec. 1978.

Birstein et al., "The Manufacture of Needle Type Si(-Li)Detectors for Biomedical Use" Nuclear Instruments and Methods vol. 133 No. 2, 1976 pp. 279-282.

Holmes-Siedle, "The Space-Charge Dosimeter" Nucl. Instru. and Methods vol. 121 pp. 169-179 1974.

Friedland et al., "Invivo Silicon Detectors, Invivo-preamplifiers and Their Applications", IEEE Trans Nucl. Sci. vol. NS-19 No. 3 Jun. 1972.

*Primary Examiner*—Ruth S. Smith
*Attorney, Agent, or Firm*—Karla Ojanen; James H. Chafin; William R. Moser

[57] ABSTRACT

Methods of and apparatus for in vivo radiation measurements relay on a MOSFET dosimeter of high radiation sensitivity with operates in both the passive mode to provide an integrated dose detector and active mode to provide an irradiation rate detector. A compensating circuit with a matched unirradiated MOSFET is provided to operate at a current designed to eliminate temperature dependence of the device. Preferably, the MOSFET is rigidly mounted in the end of a miniature catheter and the catheter is implanted in the patient proximate the radiation source.

5 Claims, 6 Drawing Sheets

METHODS OF IN VIVO RADIATION MEASUREMENT

This is a division of application Ser. No. 901,867 filed Aug. 29, 1986 now abandoned.

The instant invention relates to methods of and apparatus for radiation measurement; more particularly, the instant invention relates to methods of and apparatus especially suitable for in vivo radiation measurement wherein a miniature dosimeter in the form of a metal oxide semiconductor field effect transistor (MOSFET) is implanted proximate a radiation source.

GENERAL CONSIDERATIONS AND PRIOR ART

The use of ionizing radiation from various sources to treat tumors is wide-spread. Each year some 250,000 people undergo radiation therapy. At present it is not common practice to instrument a patient with dosimeters, although passive dosimeters such as thermal luminescent dosimeters (TLDS) are available. To date, no miniature devices are available for in vivo, real time dosimetry of patients. Generally, the dose delivered to a patient is determined from computer modeling in conjunction with calibration of radiation sources. It would of course be more desirable to have a device which could be implanted within the patient so as to give a direct read-out of the dose to the patient's tissue while the radiation is being applied. Such an approach would both minimize mistakes in the total radiation dose given to a patient and provide for more accurate dosages. Moreover, data accumulated from many patients will eventually allow oncologists to make more accurate appraisals of the most effective dosages for various types of tumors. To date, the prior art does not provide such devices.

Historically, miniature radiation detectors utilized gas filled ionization chambers, as is exemplified by U.S. Pat. No. 3,297,896 to Anton. These devices have a relatively low sensitivity, are relatively expensive to fabricate and require high operating voltages. In addition, they necessarily measure only the rate of radiation exposure and not a cumulative, integrated dose. In medical determinations, the cumulative integrated dose is of considerable importance. The use of solid-state devices as dosimeters is disclosed in numerous patents, for example, the patents to Kobayshi, U.S. Pat. Nos. 3,670,719, 3,598,109, 3,665,916 and U.S. Pat. No. 3,669,095. In each of the Kobayshi patents, PN juction detectors are utilized, however, in each case, the detectors do not integrate the exposure so as to give a cumulative dose and in each case the detectors require an applied voltage. While the applied voltage is certainly less than the 300 to 3,000 volts required by the gas filled tube of U.S. Pat. No. 3,297,896 to Anton, substantial applied voltage is nonetheless required. In the case of U.S. Pat. No. 3,598,109 to Kobayshi, the voltage required is on the order of 10-30 volts, which voltage could possibly be hazardous. Other patents, such as U.S. Pat. No. 3,429,454 to Webb, and U.S. Pat. No. 4,152,595 to Garfinkle are further illustrative of prior art approaches relying on PN junction detectors with substantial applied voltage.

U.S. Pat. No. 4,484,076 to Thomson discloses a MOSFET device utilized as a radiation detector while the article, R.C. Hughes, Theory of Response of Radiation Sensing Field Effect Transistors, J. Appl. Physics, 58(3), page 1375 (Aug. 1985), discloses the use, of a MOSFET device as a radiation detector. Moreover, Thomson does not specify the use of isothermal current value in order to eliminate temperature dependence of the device or how the device is used in vivo.

In view of the need for readily available in vivo dosimeter devices and in view of the deficiencies of the aforementioned prior art devices, there is a need for an improved in vivo dosimeter device.

SUMMARY OF THE INVENTION

It is an object of the instant invention to provide new and improved methods of radiation measurements.

In view of the aforementioned object, the instant invention contemplates a method of radiation measurement wherein the method comprises the steps of inserting a radiation sensitive MOSFET in a patient and continuously monitoring the implanted MOSFET while comparing the gate voltage thereof with the gate voltage of a reference MOSFET in order to measure the rate of radiation exposure.

An additional method comprises the steps of calibrating a radiation sensitive MOSFET, inserting the MOSFET in the body of a patient adjacent an area to be irradiated and after a period of time measuring the threshold voltage of the MOSFET to determine the change in threshold voltage as a result of irradiation of the MOSFET. This measurement corresponds to the total radiation dosage accumulated over a period of time.

DESCRIPTION OF THE PREFERRED EMBODIMENT

Figure 1:
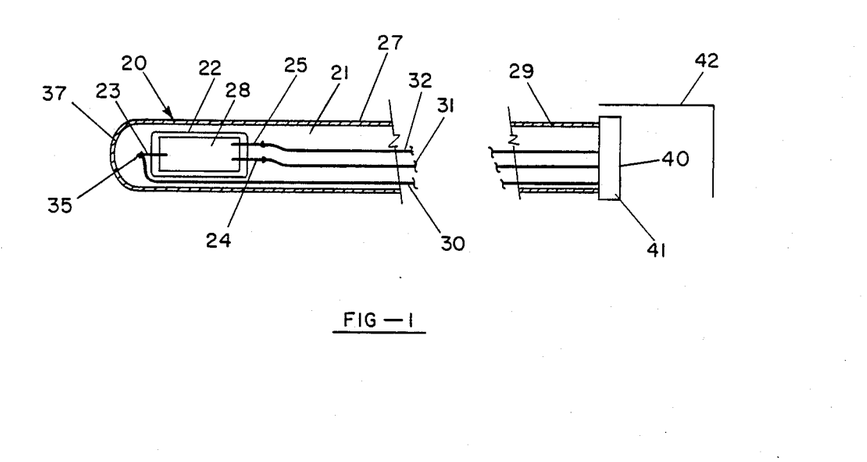
FIG. 1 is an enlarged prospective view of a chip-carrier for use in a catheter configured to carry a MOSFET chip in accordance with the principles of the instant invention.

Referring now to FIG. 1 wherein there is shown a probe designated generally by the numeral 20, which comprises an elongated chip carrier or header 21 upon which is mounted a chip 22. The chip 22 has three leads 23, 24, 25 extending therefrom for exterior monitoring of the chip 22.

The chip 22 includes an active device in the form of a metal oxide semiconductor field effect transistor (MOSFET) 28 which, for purposes of this discussion, is referred to as a RADFET (radiation sensing field effect transistor). As will be further explained hereinafter, the RADFET 28 can be used in either an active or a passive mode. Lead 23 is the gate lead, lead 24 is the source lead and lead 25 is drain lead.

Since there are no chip carriers commercially available which are small enough to fit inside an 8 millimeter (outside diameter) catheter tube, the inventors of the instant device configured a catheter tube 29 specifically suited to the purposes of the instant invention. This was accomplished by cutting the end of the catheter tube 29 in half along its length and bringing three insulated leads 30, 31 and 32 of #38 wire through the catheter tube to the cut section. A layer of epoxy is used to provide the chip support 21 and also to secure the insulated leads 30, 31 and 32 within the catheter with the source and gate connections combined. Before bonding the chip 22 to the platform 21, the insulated leads 30,31 and 32 are secured thereto with Hartman epoxy for mechanical strength, while the chip leads 23, 24 and 25 are bonded to the chips 22 with a conductive silver-loaded polyimide. Both the epoxy and conductive silver-loaded polyimide are cured at 150° C. for 30 minutes. The leads 23, 24 and 25 are secured to the insulated leads 30, 31 and 32 respectively by silver-loaded polyimide after the chip and wire bonds are stabilized with 3-minute epoxy. Subsequent to testing for continuity, the end 39 of the catheter 29 is sealed with 3-minute epoxy so as to conform the end of the catheter to the shape of the original catheter.

In order to avoid unnecessary stress on the wires, the other end of the catheter 29 is epoxied in a Swagelock fitting 41 inside of a connection box 42. Leads from exterior equipment are then connected through the connection box 41 to the insulated leads 30, 31 and 32. Consequently, pulling or bending of the catheter 29 does not directly stress either the chip leads 23, 24 and 25 on the insulated leads 30, 31 and 32 since the stress is absorbed by the tubular body of the catheter 29.

The probe 20 shown in FIG. 1 is configured specifically to be compatible with radiation implant technology already practiced for treating tumors in breasts and prostates. Briefly, in the procedure for the implant, the area to be irradiated is pierced with hollow metal needles and a four millimeter plastic catheter is threaded through or is placed in each metal needle. The metal needles are then removed and the hollow plastic catheters allowed to remain in place. Radioactive pellets contained in a one millimeter (outside diameter) catheter are inserted through the implanted four millimeter catheters to commence the tumor irradiation. Typically, the irradiation lasts two days with a dose to the tumor of about 2,000 rads. Both the four millimeter and on millimeter catheters are then removed. Since the radiation has killed the tissue around the catheter, there is little danger of spreading the cancer cells by removing the catheter.

Figure 2:
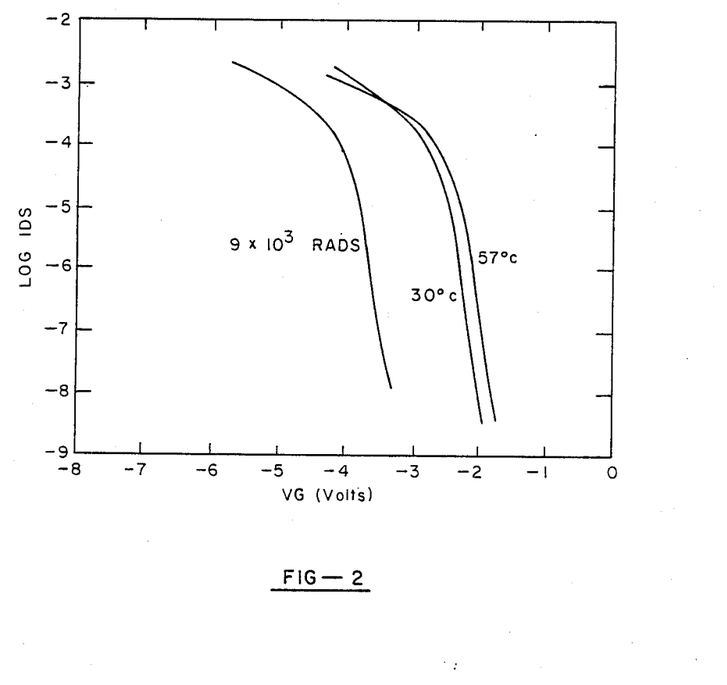
FIG. 2 is a graph showing the current-voltage characteristics of MOSFETS used as radiation detectors in accordance with the principles of the instant invention.

In accordance with the instant invention, the RADFET 28 is generally configured as a typical MOSFET. Since the RADFET 28 is set up as a three-terminal device, it can be conceptualized as a voltage controlled resistor. As is seen in FIG. 2 (in conjunction with FIG. 3) if a constant voltage from a battery or a power supply is put on one terminal (the drain 50), a current will flow between source 51 and drain 50 which is dependent on the voltage from an independent battery or power supply placed on the third terminal (gate 53). Virtually no current is drawn from the power supply by the gate 53.

The particular MOSFETS which are used as RADFETS in accordance with the principles of the instant invention have the characteristics displayed by the curve shown in FIG. 2. In FIG. 2, the drain 50 is held at −5 volts while the voltage gate (VG) on gate 53 is varied. It can be seen that almost no current (IDS) flows when the gate voltage is held at zero volts and that meaningful conduction does not begin until about −2 volts is placed on gate 53. A device having these characteristics in known as an enhancement mode, P-channel MOSFET.

The slope of the current-voltage plot is known as the transconductance of the MOSFET, and the threshold voltage ($V_{th}$) plotted in FIGS. 4,5,7 and 9 is loosely defined by extrapolating a straight line back along the current voltage curve to 0 current which in this case is a gate voltage of about −2.3 volts. The threshold voltage ($V_{th}$) could also be defined as the voltage required to create a certain current (e.g., 10 microamps), however, one must be consistent in the definition used when measuring the small changes in threshold voltage ($V_{th}$) which occurs upon exposure of the RADFET to radiation.

For a number of years, it has been known that certain kinds of MOSFETS are sensitive to ionizing radiation. Accordingly, considerable effort has gone into "hardening" MOSFETS in order to make them insensitive to radiation. The most common radiation effect is that the silicon dioxide insulating layer between the gate and the silicon surface acquires a net positive charge from the ionizing radiation. The threshold voltage must then be shifted to a more negative value in order to compensate for the positive charge in the oxide so as to maintain the same current from drain to source. The net effect is to translate the current voltage characteristics shown in FIG. 2 to more negative values without changing the shape of the curves. The curve of FIG. 2 is translated 1.3 volts negative by a dose of 9,000 rads.

Charging of the silicon dioxide results because there are many more hole traps than electron traps in "unhardened" silicon dioxide. The ionizing radiation creates equal number of free electrons and holes, but if the electrons drift or diffuse out of the silicon dioxide, while the holes are trapped, the net charge of the trapped holes remains in the silicon dioxide. These hole traps can be induced into the MOSFET gate oxide by particular processing steps. For example, an anneal in a nitrogen atmosphere at a high temperature on the order of 1,100° C. will introduce hole traps. One may also utilize ion implantation of the silicon dioxide to introduce hole traps and to provide a way of softening one MOSFET on a chip while leaving all the others hardened Accordingly, RADFETS 28 can be fabricated in any silicon micro-electronics facility if the processing of the device is very carefully controlled. One RADFET 28 used for the instant invention is an inexpensive commercial MOSFET known as the Intersil 3N161 which is inadvertently soft to radiation due to the manufacture's processing steps. This particular RADFET is stable and rugged with an adequate low-dose response. The Intersil 3N161 utilizes aluminum gate metallization so that any ionizing radiation which is perpendicularly incident to the RADFET passes through only the epoxy potting compound, the glass protection layer (which is only a few microns thick), and the metal of the aluminum gate before reaching the gate dielectric. There are no metals of high atomic number in the path of this radiation. The gate dielectric consists of a thermally grown silicon dioxide active layer 180 nm thick covered with a 62 nm layer of silicon nitride. The silicon nitrite layer helps prevent ion contamination of the oxide and appears to play no role in the radiation response.

While the Intersil 3N161 MOSFET has the proven satisfactory as a RADFET 28, the instant invention further includes the concept of fabricating a RADFET 28 by utilizing a gate metal with a high atomic number (Z) such as platinum. Gold or palladium might also work, but they adhere less well to silicon dioxide. The increased sensitivity resulting from using a RADFET with a high atomic number is the result of dose enhancement and work function effects. Any time there is an interference between a high Z material and a low Z material, such as the interface between platinum and silicon dioxide, with ionizing radiation passing across the interface, the energy deposited by the radiation is higher in the high Z material. Because of the proximity of the low Z material, the dose to it is enhanced. The enhancement can be increased by a factor of ten depending on the energy of the radiation and the thickness of the layers. There are computer programs for predicting enhancement and some experimental confirmation exists for the effect caused by gold metal in the header over the RADFET (IEEE, NS 30, page 4388, 1983). Platinum gated RADFETS have to be carefully calibrated for each kind of radiation in order to provide an accurate dosage reading.

When RADFETS are operated without an external bias, the sensitivity is lower because there is little if any electric field in the active oxide layer to help separate the electrons and holes created by impinging radiation. Since aluminum gate metal on a silicon nitride layer has a very small work function, no electric field exists in the oxide. On the other hand, platinum has about a one volt higher work function than aluminum and will place a field in the oxide which corresponds to about minus one volt on an aluminum gate. This effect will be especially strong for thick oxide devices wherein the electron lifetime prevents electrons from diffusing out of the oxide.

Figure 11:
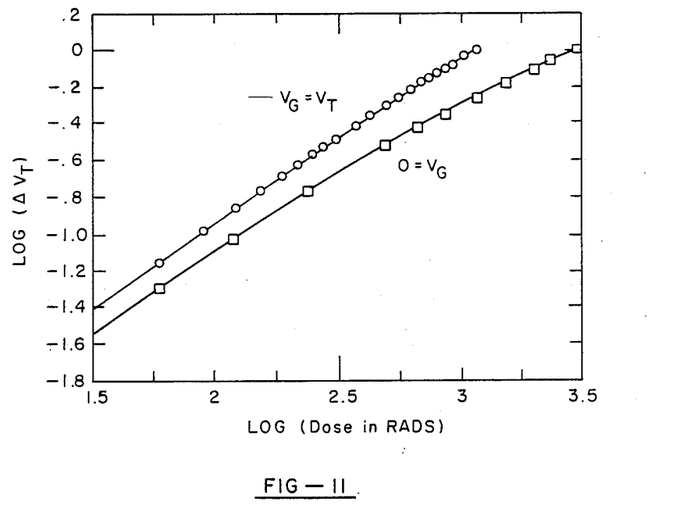
FIG. 11 is a graph correlating the log of change in voltage as a function of the log of radiation dosage in rads.

Referring now to FIG. 11, by using a platinum electrode, the bottom curve of the Figure could be raised to the upper curve resulting in an improvement factor of approximately two. The saturation of a RADFET using platinum electrodes occurs at a lower voltage than for a similar RADFET using an aluminum gate. This is due to the sign of the field in the silicon dioxide which is caused by the work function of the platinum electrode. To obtain higher sensitivity at higher doses, one would use a lower work function metal such as aluminum and an n-channel FET (i.e., on p-type silicon).

Figure 3:
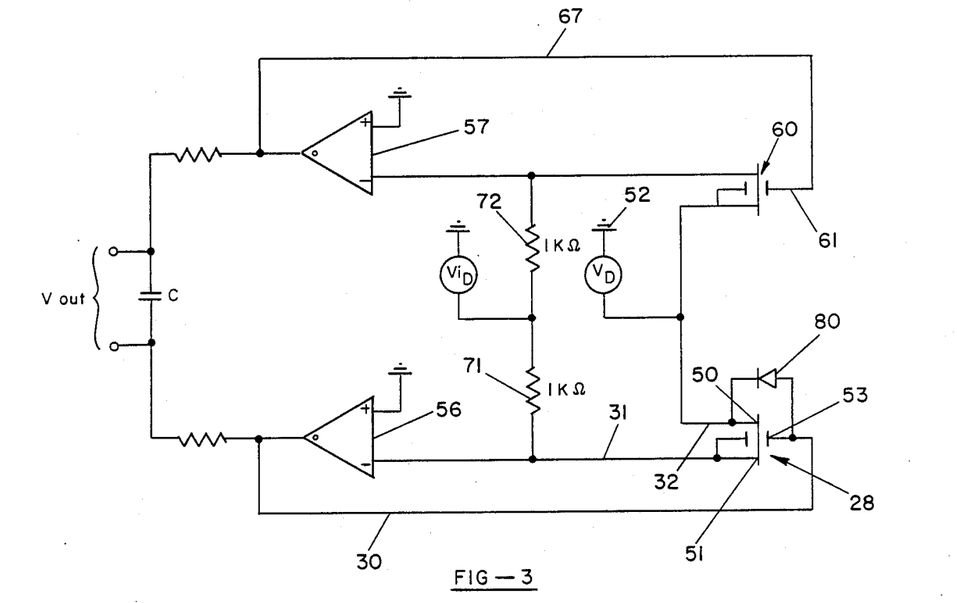
FIG. 3 is a circuit diagram of a differential MOSFET control and measurement circuit configured in accordance with the principles of the instant invention.

In order to improve the stability of the RADFET measurement, the measurement and control circuit of FIG. 3 comprises a compensation portion including MOSFET 60 and operational amplifier 57, and a sensing/measurement portion including RADFET 28 and operational amplifier 56. Source 51 of RADFET 28 is connected through line 31 to the input of operational amplifier 56, the = input of the amplifier being connected to ground. The output of operational amplifier 56 is fed back through line 30 to gate 53 of RADFET 28. In operation, if the voltage at line 31 becomes more positive than the zero volts on the = input, the output of amplifer 56 becomes more negative, and the gate voltage of RADFET 28 also goes more negative, causing the potential at source 51 of the p-channel MOSFET (RADFET) to go more negative, thereby making the voltage at line 31 less positive. Conversely, if the voltage at line 31 becomes more negative than zero volts, the output of amplifier 56 and the gate voltage of RADFET 28 both become more positive, causing the potential at source 51 to go more positive, thereby making the voltage on line 31 less negative. Accordingly, the voltage at line 31 is maintained by this process of negative feedback at a value very close to zero volts.

Resistor 71 is connected at one end to a voltage source $V_{ID}$ and at the opposite end to line 31. By Ohm's Law, the current through this 1 kΩ resistor is a constant determined by the value of $V_{ID}$. Since the current flowing into operational amplifier 56 is negligible, this constant current must flow through the source and drain connections of RADFET 28. Drain 50 of RADFET 28 is connected through line 32 to a voltage source $V_D$ to maintain a constant drain voltage whereby RADFET 28 is properly biased to conduct the constant current for a predetermined gate voltage.

When radiation impinges on RADFET 28, the characteristics of the dielectric material located under gate 53 change, as discussed herein, whereby a new value of gate voltage is required to maintain the drain voltage and source-drain current constrained by the configuration of the circuit. The output of amplifier 56 fed back on line 30 provides this voltage to RADFET 28. The changes in this voltage at the output 75 of the circuit of FIG. 3 provide an indication of the changes in the RADFET caused by impinging radiation. The circuit of FIG. 3 utilizes a reference RADFET 60 connected in a manner identical to measuring RADFET 28 to measure" the difference in gate voltages between the radiated RADFET 28 and the reference RADFET 60. Since RADFET 60 is mounted away from RADFET 28 and, therefore, receives no radiation, amplifier 57 produces an output which varies in response to thermal or other drift and which is subtracted from the output of amplifier 56 at circuit output 75. The circuit compares the voltage on line 30 with that on line 61 by monitoring the output of amplifiers 56 and 57. This provides for very sensitive measurement wherein one microvolt change in the gate voltage of RADFET 28 provides a voltage difference which corresponds to about one millirad of a radiation dose. The arrangement also removes any long-term drift since the drift is the same in both devices. The RADFET 28 is in the radiation environment while the RADFET 60 is shielded from the radiation as is with the rest of the electronics. The drain to source current is selected to minimize changes in gate voltage due to temperature changes. For each pair of RADFETS 28 and 60, the current must be found experimentally. Generally, the applicants have found the current of about 700 microamps to be the proper point. Operating in this mode, there is less than a one millivolt change in the gate volt difference when the active RADFET 28 is brought from room temperature up to body temperature (approximately 36° C.) while the shielded RADFET remains at room temperature (approximately 20° C).

In a typical circuit, R might have a value of 5K and C a value of 100 uF resulting in about a one second response time for the output voltage $V_{out}$.

Figure 7A:
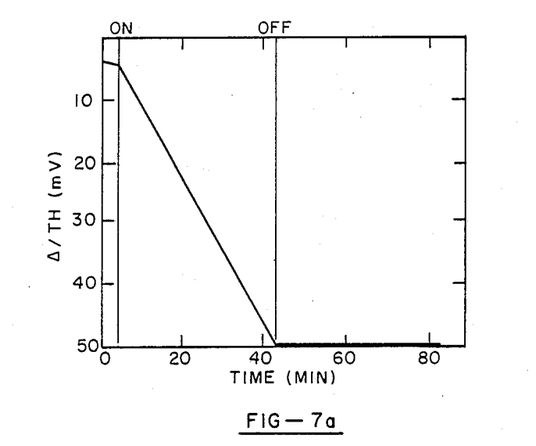
FIGS. 7A, 7B and 7C are graphs plotting changes in threshold voltage and millivolts as a function of time for various temperature levels.
Figure 7B:
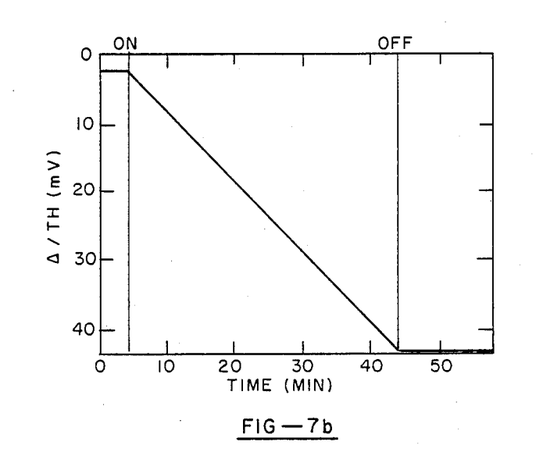
Figure 7C:
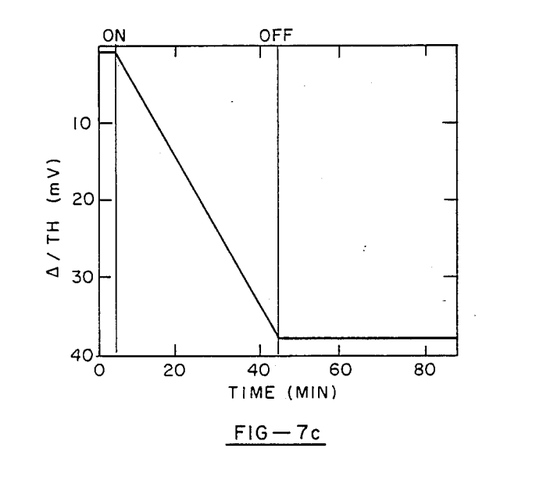

Thus far, RADFET 28 has been described as functioning in a manner analogous to a simple voltage controlled resistor. However, in order to use the RADFET 28 as a high accuracy dosimeter, one must take into account the physics of MOSFETS in general. As is seen in FIG. 7, the voltage curves change shape at different temperatures. Thus, changing the temperature of one RADFET 28 while holding the reference RADFET 60 at a constant temperature can change the output voltage. Since this is a reproducible characteristic, accurate measurement of the local temperature allows correction of the data for changing temperature.

The chip for the Intersil 3N161 includes a diode 80 for protecting the gate from static charging. The current through this diode at a fixed bias is a function of the absolute temperature. Thus a temperature measuring device already exists in the chip. In practice, self-compensation for temperature is easier to accomplish. As is seen in FIG. 2, the current voltage characteristics for two different temperatures intersect at about 700 microamps. If the device is operated at a current level of about 700 microamps, the threshold voltage ($V_{th}$) has less then one millivolt temperature dependence between 20° C. and 40° C. This phenomena is also true for devices which have had some previous radiation exposure. The existence of this isothermal point at 700 microamps is that there are two competing effects which change the threshold voltage ($V_{th}$), one relating to the fermi level in the silicon and the other with the change in transconductance or carrier mobility, in the channel. Fortuitously, these two effects change the threshold voltage ($V_{th}$) in opposite directions resulting in a particular channel current with zero temperature drift.

Figure 4:
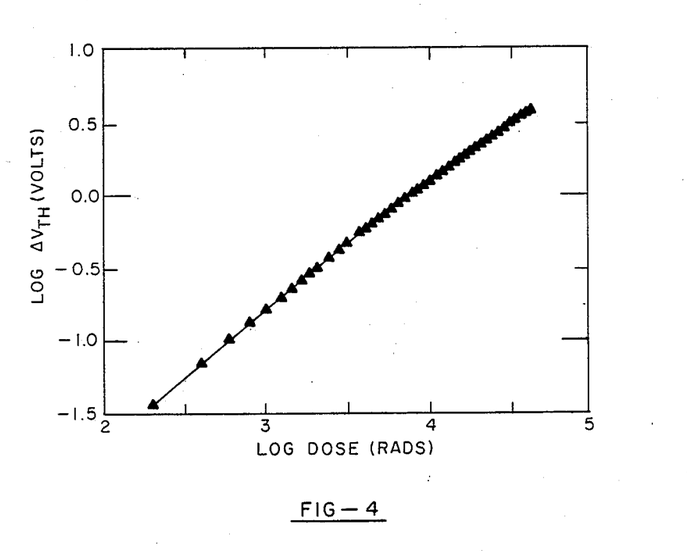
FIG. 4 is a diagram illustrating the log of voltage shift as a function of the log of radiation dosage.
Figure 5:
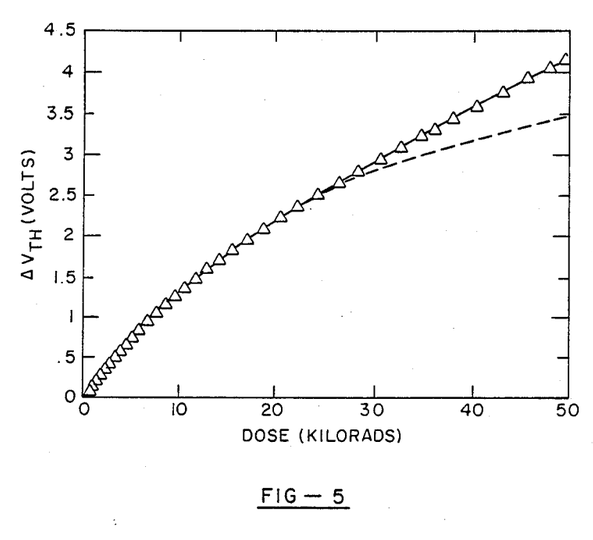
FIG. 5 is a graph plotting voltage shift as a function of dosage in kilorads.
Figure 6:
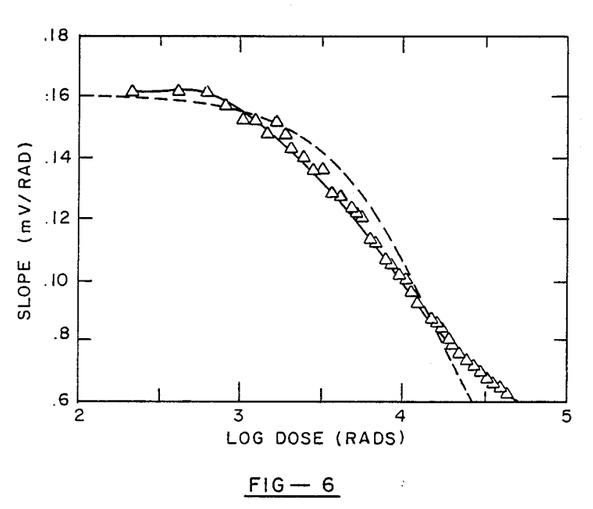
FIG. 6 is a chart plotting the slope of millivolts per rad against the log of the dosage in rads.

Referring now to FIG. 4, the log of the voltage shift ($V_{th}$) is shown as a function of the log of the radiation dosage in rads. The RADFET 28 is calibrated using a colbalt 60 source with a built-up layer of polystyrene used to provide electronic equilibrium. The source of x-rays for the data shown in FIG. 4 is a General Electric XR6 x-ray machine operating at 60 kev. The shape of the curve is independent of the x-ray energy. The circuit set forth in FIG. 3 which is used for reading the change in voltage of the RADFET 28 automatically corrects for non-linearity of the response of the RADFETS 28. However, at dosages above 1,000 rads, the sensitivity of millivolts per rad becomes monotonically smaller,. In FIG. 5, the linear dependence of the RADFET 28 is plotted as a function of the linear dose in kilorads. The uncertainties in the data taken in a digital data logger (Keithley 197), are much smaller than that shown by the size of the data point triangles. The resulting noise is less than 100 microvolts. In FIG. 6, the slope of the data expressed in millivolts per rad is plotted as a function of the log of the dosage in rads.

At much higher doses than are shown in FIG. 5, the response will saturate. Basically, the space charged due to the trapped holes causes a distortion in the internal electric field which leads to enhanced recombination of the radiation induced electrons with trapped holes. At high dosages, the process of generation and recombination reaches a steady state and no increase in the density of trapped holes occurs. Consequently, there is no further increase
5 in threshold voltage ($V_{th}$) with extra dosages.

The exact theory for the shape of the response curve shown in FIG. 5 is fairly complicated and requires numerical computer solutions. However, the following simplified analytical formula gives an adequate fit to the data:

$$\Delta V_{th} = A^*(1 - \exp(-B^* \text{ dose}))$$

wherein A equals 4.05 volts and B equals $3.93 \times 10^{-5}$ rad $-1$. The solution to this expression is shown in the dashed line of FIG. 5. The derivative of this Formula gives the sensitivity in millivolts per rad which equals $A^* B^* \exp(-B^* \text{ dose})$ which appears as the dashed line in FIG. 6. In accordance with the principles of the instant invention, the expressions are used as algorithms for a computer correction of the raw data from the voltage measuring circuit.

Referring now to FIGS. 7A, 7B and 7C, responses at $-180°$ C., 23° C. and 100° C. are shown for the same dose rate exposure in threshold temperatures per millivolt for roughly the same periods of time. As is seen in FIG. 7, these slopes are the same within experimental level. The plots of FIGS. 7A, 7B and 7C were obtained by mounting the RADFET 28 in a vacuum chamber and impinging x-ray radiation thereon from the tube of a General Electric XRD-6 x-ray machine operating at 60 keV. The flux was filtered to give a dose rate at the sample of about 0.1 rad/sec. The output of the x-ray machine as measured with a PIN diode is constant within the time frame of 1 to 2 seconds after turnon. As is readily seen, the linearity is quite constant which supports the conclusion that the RADFET 28 is adequate as a dosimeter over a very wide temperature range without correction of the data as long as the RADFET 28 is utilized with a temperature compensating circuit such as the circuit of FIG. 3.

Figure 8:
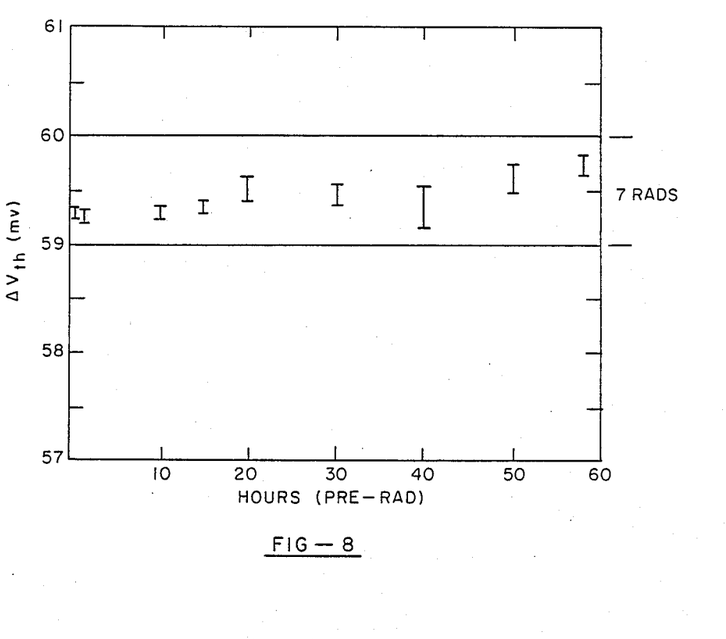
FIG. 8 is a graph plotting variations and voltage as a function of time before the application of radiation to the dosimeter.

Reading of the radiation dose received by the RADFET 28 is essentially a DC voltage measurement which is subject to drift. A drift in the threshold voltage $V_{th}$ over a period of days, for example, would limit the accuracy of the dose which could be read over that time period. The differential circuit of FIG. 3 has substantially improved the stability of the RADFET for reading very low dose rates over a period of days. Referring now to FIG. 8, there is shown data logged on a 5-digit digital volt meter over 60 hours before the RADFET 28 has received any radiation dose. The arrow bars in the FIG. 8 indicate the maximum and minimum voltage readings in the adjacent period. Since a one millivolt change indicates about 7 rads total dose, an accumulated dose of 7 rads or more could be accurately measured over a 60 hour period. About one order of magnitude more accuracy is available if one is only interested in a time frame of a few minutes because of the differences between noise and drift. When measuring very small changes in DC voltage, one must be concerned with other sources of drift, such as the volt meter becoming uncalibrated, failure of the circuit elements in the differential circuit, discharge of the batteries if the unit is battery powered and series resistances in the contacts as well as intrinsic drift of the devices themselves. Careful electronics practice can avoid most of these problems and the low drift data as is seen in FIG. 8 is routinely obtained. By utilizing other types of RADFETS 28 having thicker gate dielectrics, the sensitivity in millivolts per rad increases as the square of the dielectric thickness by virtue of increases in volume and capacitance.

Figure 9:
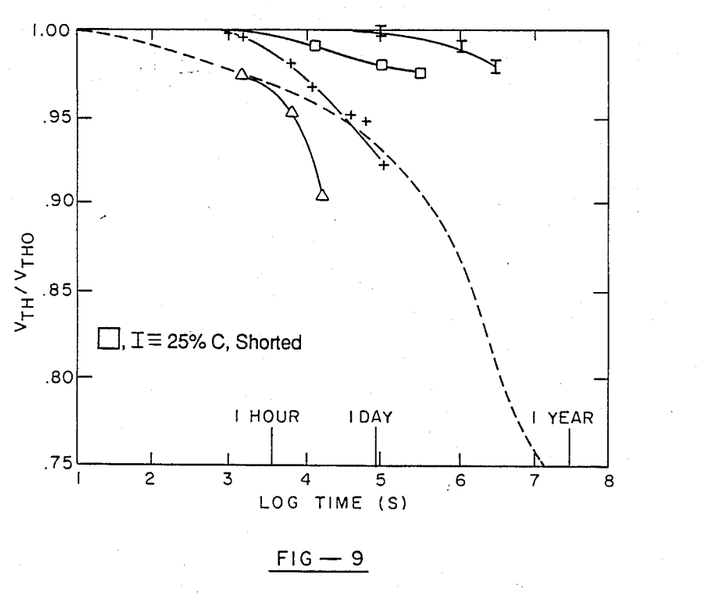
FIG. 9 is a graph plotting decay of the voltage shift as a function of log time.
Figure 10:
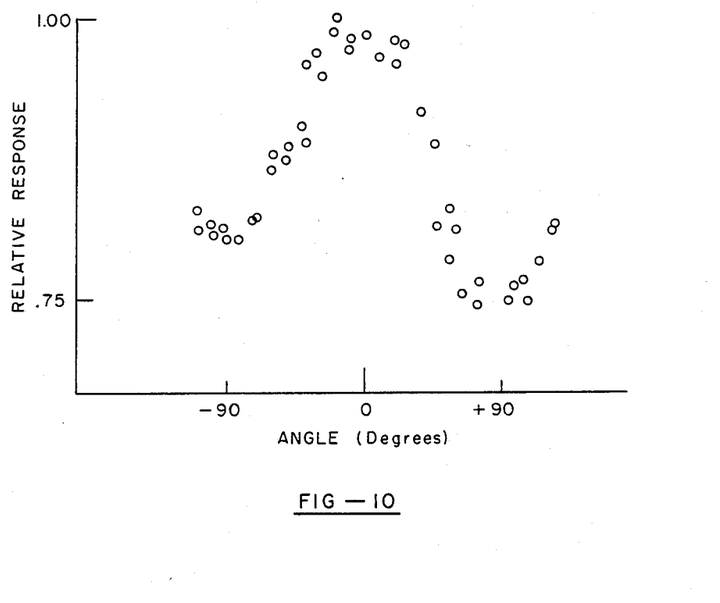
FIG. 10 is a graph correlating the position of the chip with respect to the direction of flux from the radiation source.

As is seen in FIG. 9, the radiation induced changes in the threshold voltage of the RADFET 28 are stable within the noise range for several minutes after the impingement of radiation is stopped. However, if the voltage is monitored for many hours and days after the radiation is stopped, there is some decay of the threshold change. FIG. 9 illustrates typical data wherein the change is normalized to the maximum since it is found that fractional loss is proportional to total dose. In FIG. 9, the linear fractional decay rate is plotted as a function of log time in seconds. The decay is different depending upon the shift and whether it is monitored continuously or whether the RADFET 28 is shorted during the time during measurements. The recorded shift decays only a few percent over several years if the RADFET 28 is left in a shorted condition and near room temperature. If the radiation is carried out at a higher temperature and the RADFET is left at the higher temperature, the decay is faster. Data for a run at 100° C. is given in FIG. 8. At 100° C. there is a temperature dependence to the gate voltage which accounts for the large error bars. The circuit parameters which eliminate the temperature dependence in the 0°–50° C. range do not work at much higher temperatures. The permanent record of the dose in the shorted RADFET 28 makes it possible to store used RADFETS 28 for future reference if necessary. Similar long-term storage behavior has been reported by Holmes-Seidle for RADFETS in European satellites and earth bound simulations (see A. Holmes-Seidle et al Calibration and Flight Testing of Low Field Effect P-MOS Dosimeter IEEE, Trans. Nuc. Sci. NS-32 (Dec. 1985)).

The decay of the voltage shift can be quantitatively understood in terms of the very slow motion of the trapped holes. This phenomena has been studied in detail in silicon dioxide which has been hardened and is often referred to as "dispersive transport". One of the most interesting features of this model is that it predicts the experimental observation that holes move slower as time passes. Consequently, the data is plotted against the log of time. An approximate solution to the decay is shown in the solid line in FIG. 9 and has the analytical expression:

$$V_{th}/V_{tho} = 1 - AT^{2\alpha}$$

wherein $\alpha$ is a parameter in the dispersive transport theory with a value of about 0.2 and A is a constant which includes the electric field, temperature and trapping distribution. In this particular case, A is an empirical constant determined from the data of the particular type of RADFET 28. Other methods of preparing silicon dioxide will provide a different value for A; in particular, hardened oxides will have A values several orders of magnitude higher than unhardened oxides at the same temperature.

As is seen in FIG. 9, at temperatures much higher than 100° C., the decay is fast enough to make it possible to erase the voltage shift. A few hours at 250° C. is enough to bring the RADFET 28 almost back to its initial unradiated condition, after which it will respond to radiation at room temperature in a manner similar to an unused device. However, these temperatures are destructive to the polymeric materials used in the catheter probe 20. The inexpensive nature of the catheter probe 20 renders it unnecessary to recycle catheters after initial use.

In order to produced reproducible RADFETS 28, it is necessary to have detailed control over the processing thereof. In particular, high temperature aneeling an impurity control is required. Otherwise, calibration of each RADFET 28 will be necessary. Fortunately, such calibration can be easily and inexpensively be performed by exposing the RADFET to a small dose of radiation, for example 100 rads from a calibrated source.

A RADFET 28 disposed in a catheter probe 20 is not a completely isotropic device. This is because of the silicon chip 22 itself, metallic leads, and high Z materials used as ohmic contacts at the bottom of the silicon chip. Any of these structures can produce a change in the actual radiation dose received by the active silicon dioxide as a function of the direction of the x-ray flux. It has been found that there is roughly a 25% loss in sensitivity from the most sensitive angle to the least sensitive angle. Accordingly, for accurate dosimetry, the position of the chip 22 with respect to the source of radiation must be known.

A chief advantage of using a RADFET 28 as a dosimeter is that continuous readings of the accumulated dose are available by utilizing the tracking gate circuit of FIG. 3. By using simple differentiation with a small computer, the dose rate is available immediately. At very low dose rates, the computer would have to wait for the threshold voltage ($V_{th}$) to change by approximately one millivolt before calculating the dose rate in order to be above the noise level and to obtain an accurate reading. Moreover, another advantage of the RADFET 28 utilized in accordance with the principles of the instant invention is that it is non-volatile. In other words, it does not forget the accumulated dose if the power is cut off or the batteries run down. The RADFET 28 continues to record dosages when the RADFET is shorted out. For some uses, it may be desirable to use the RADFET without a power source. In other words, at either zero volts or shorted. The RADFET 28 can be exposed to radiation in the shorted condition and then returned to the voltage threshold unit and the accumulated dose measured. The results of such an experiment are shown in FIG. 11 where it can be seen that the sensitivity for the $0 = V_G$ curve is less, but the response is still fairly linear with respect to the dosage when one compares the $0 = V_G$ curve with the $V_G = V_T$ curve. Parameters for the dash line formula of FIG. 5 are different for the 0 volt irradiations.

There is evidence that the number of electron hole pairs produced in silicon dioxide per rad dose deposited is independent of x-ray energy down to very low energies on the order of 1 keV. This is because no radiation damage in the form of displacement of atoms is required for the charging effect and is similar to the photocurrent produced in a well-characterized silicon photodiode. However, there are differences in the response to lower energy x-rays for at least two reasons. The first reason is that the actual x-ray flux at the silicon dioxide level will be attenuated or enhanced by the materials surrounding it. For example, if the aluminum gate is replaced by a high atomic number (Z) gold gate, low energy x-rays would place a much larger dose in the gold than in the aluminum with some of that higher dose leaking over into the silicon dioxide and creating dose enhancement. However, a very thick gold layer would attenuate the flux before it reached the silicon dioxide. These types of effects have been measured on RADFETS such as the RADFET 28 and the results can be understood from radiation transport computer codes as is set forth in the article by J. G. Kelley et al, IEEE, Trans. Nuc. Sci. NS-30, 4338 (1983). In this particular application, the effects can be understood and compensated for most easily by careful calibration of the type of x-ray and material environment expected in use. RADFETS have an advantage over other dosimetric methods in that the active region is very thin (on the order of 180 nm) and does not itself attenuate even very high linear energy transfer radiation. For improved performance with low energy x-rays it is also possible to fabricate RADFETS with all low atomic number (Z) materials like aluminum.

The small size, flexibility and ruggedness of the RADFET 28 in a catheter probe 20 make it convenient for monitoring radiation dosages in many areas that were previously inaccessible. Moreover, the catheter proble 20 can be inserted anywhere in the body without fear of electrical problems. This is especially the case when using the battery powered unit.

The particular catheter probe 20 chosen for mounting the RADFET 27 is also the same type of catheter which is used for inserting radioactive seeds into the body for irradiating tumors. This treatment is in wide use for interstitial irradiations of breast, prostate and cervix tissue.

EXAMPLE OF USE

A typical treatment protocol includes the following steps. (1) The tissue to be irradiated is penetrated by hollow metal catheters through which four millimeter plastic catheters are threaded. The metal catheters are removed, but the plastic catheters remain for the duration of the treatment. In a typical breast irradiation, there may be 10 plastic catheters inserted. (2) The radioactive seeds are contained in a 0.8 millimeter outside diameter catheter at 1 cm spacings and are kept in a lead "pig" before treatment. When treatment commences, the radioactive pellets are threaded through the larger catheters already in place. (3) The irradiation typically lasts for two days with doses to the tissue in the range of 2,000 rads. (4) After treatment, both catheters are removed. Since the radiation has killed tumor tissue close to the catheter, there is little danger of spreading the cancer by mechanical motion of catheter removal.

The RADFET 28 in a catheter probe 20 is designed to be placed anywhere the radioactive pellets can be placed, without additional surgery or trauma to the patient. Thus, one of the ten catheters could be used for the RADFET 28. This catheter could be monitored immediately to see if the dose rate calculations for the numbered position of radioactive pellets is correct. The catheter probe 20 can identify pellets which are either more or less radioactive than anticipated and it can prevent mistakes of either over-irradiating or under-irradiating the patient for a variety of reasons.

For pellet irradiations which involve surgical implants rather than catheters, the RADFET 28 can be inserted into the closest possible tissue. For example, for implants of the prostate, the RADFET 28 and a catheter probe 20 could be inserted in the urethra as far as the prostate. The dose rate is monitored for a couple of hours to see if the implant is correctly done. At a later time, the dose rate is monitored to see if the radioactive decay of the implants is on schedule.

The RADFET 28 in a catheter 20 is small enough to be fed through a vein or artery so as to approach an internal tumor which is being irradiated from the outside with, for example, cobalt 60. Consequently, the reluctance on the part of some physicians to disturb a tumor by inserting a radiation monitor therein can be overcome by simply feeding the catheter through a vein or artery.

Due to the small size of the RADFET 28 and the catheter probe 20, a plurality of catheters are readily combinable for array sensing. In addition, with appropriate flexible chip carrier technology, several RADFETS 28 can be spaced along the flexible chip carrier. In order to minimize the number of leads coming out of a catheter probe 20, additional circuit elements could be used to multiplex the voltages on each RADFET 28. Finally, for higher dose levels any multiplexing transistors among the additional circuit elements next to RADFET 28 could be radiation hardened for protection from the applied radiation.

In summary, the aforediscussed dosimeter is smaller than those presently available and utilizes catheters employed for radioactive implants with no additional surgery. The dosimeter is mechanically rugged and insensitive to electrical noise. Doses at the ten rad level can be obtained over several days, while absolute doses in the range above one thousand rads can be obtained within a few percent accuracy. Data on both the dose rate and total dose is obtainable and, if desired, the total dose information can be kept for several years with no applied power due to the non-volatile memory of the RADFET 28.

From the foregoing description, one skilled in the art can easily ascertain the essential characteristics of this invention and without departing from the spirit and scope thereof, can make various changes and modifications of the invention to adapt it to various usages and conditions.

What is claimed is:

1. The method for in vivo monitoring of radiation applied to a patient, the method comprising the steps of:
    placing a radiation source at a fixed location inside the patient's body;
    inserting a radiation sensitive MOSFET inside the patient's body in close proximity to said radiation source, said MOSFET having a threshold voltage that changes in accordance with the cumulative radiation dosage;
    removing said MOSFET from the body after a period of radiation; and
    measuring the change in threshold voltage caused by the radiation from said source after said MOSFET has been removed from the body.

2. The method of claim 1 further including the step of placing a catheter in the patient, the MOSFET being inserted into the patient's body through said catheter.

3. The method of claim 2 further comprising the step of:
    calibrating the MOSFET prior to said step of inserting the MOSFET in the body of a patient adjacent an area to be irradiated, and
    after a period of time, removing the MOSFET and measuring the threshold voltage thereof to determine the change in threshold voltage as a result of the irradiation and to thereby determine the total radiation dosage over the time period.

4. The method of claim 3 further comprising the steps of electrically shorting the MOSFET before said period of radiation; and
    disconnecting the electrical short after said period of radiation and prior to measuring the threshold voltage of said MOSFET.

5. The method of claim 4, further including the step of comparing the radiation sensing MOSFET to an identical reference MOSFET which has not been subjected to irradiation by matching the gate voltages thereof in a comparative circuit.

* * * * *